(12) United States Patent
Erickson et al.

(10) Patent No.: US 7,955,374 B2
(45) Date of Patent: Jun. 7, 2011

(54) MODULAR BRANCH VESSEL STENT-GRAFT ASSEMBLY

(75) Inventors: David R. Erickson, Memphis, TN (US); Prema Ganesan, San Francisco, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1116 days.

(21) Appl. No.: 11/219,353

(22) Filed: Sep. 2, 2005

(65) Prior Publication Data
US 2007/0055350 A1   Mar. 8, 2007

(51) Int. Cl.
*A61F 2/06* (2006.01)
(52) U.S. Cl. ............... 623/1.16; 623/1.11; 623/1.35
(58) Field of Classification Search ........... 623/1.11, 623/1.16, 1.23, 1.35, 1.36, 1.21
See application file for complete search history.

(56) References Cited

U.S. PATENT DOCUMENTS

| | | | | |
|---|---|---|---|---|
| 5,683,449 A * | 11/1997 | Marcade | .................. | 128/898 |
| 6,059,824 A * | 5/2000 | Taheri | ................... | 623/1.15 |
| 6,383,213 B2 * | 5/2002 | Wilson et al. | ............. | 623/1.11 |
| 6,416,542 B1 * | 7/2002 | Marcade et al. | ........ | 623/1.16 |
| 6,645,242 B1 * | 11/2003 | Quinn | ................... | 623/1.16 |
| 6,660,033 B1 * | 12/2003 | Marcade et al. | ........ | 623/1.16 |
| 6,811,566 B1 * | 11/2004 | Penn et al. | ................ | 623/1.15 |
| 7,131,991 B2 * | 11/2006 | Zarins et al. | ............. | 623/1.13 |
| 7,294,145 B2 * | 11/2007 | Ward | ........................ | 623/1.11 |
| 2001/0027338 A1 * | 10/2001 | Greenberg | ............. | 623/1.13 |
| 2003/0083678 A1 * | 5/2003 | Herweck et al. | ........ | 606/153 |
| 2004/0215327 A1 * | 10/2004 | Doig et al. | ............... | 623/1.16 |
| 2005/0015135 A1 * | 1/2005 | Shanley | ................... | 623/1.11 |
| 2005/0033405 A1 * | 2/2005 | Solovay | ................... | 623/1.13 |
| 2005/0060026 A1 * | 3/2005 | Gamboa | ................... | 623/1.35 |
| 2007/0050016 A1 * | 3/2007 | Gregorich et al. | ....... | 623/1.35 |

FOREIGN PATENT DOCUMENTS

| | | |
|---|---|---|
| EP | 1470797 | 10/2004 |
| WO | WO2006/028925 | 3/2006 |
| WO | WO 2006028925 | * 3/2006 |

* cited by examiner

*Primary Examiner* — Darwin P Erezo
*Assistant Examiner* — Mark Mashack (57) ABSTRACT

Modular branch vessel stent-graft assemblies for the treatment arterial or vascular disease at the branch of two or more arteries or blood flow passageways, including, for example, abdominal aortic aneurysms are assembled in a patient's trunk/parent artery, from at least two components; a first component and a second component. The first and second components each include a first and second window, or fenestration. The second component couples with the first component by fitting at least partially in the first component to form the modular branch vessel stent-graft assembly with two selectively locatable branch openings. As the first and second components are deployed, the second component is selectively position able relative to first component so that the first and second component first and second windows overlap to form two branch openings whose longitudinal and angular positions are selectable within a range.

17 Claims, 5 Drawing Sheets

MODULAR BRANCH VESSEL STENT-GRAFT ASSEMBLY

BACKGROUND OF THE INVENTION

1. Field of the Invention

The present invention relates generally to the treatment of arterial or vascular disease at the intersection of two or more arteries or blood flow passageways, including, for example, abdominal aortic aneurysms or occlusive disease, and more particularly to a method and structure for treatment of abdominal aortic aneurysms with little or no aortic neck length below at least one of the renal arteries.

2. Description of the Related Art

In the prior art, treatment of arterial disease at the intersection of two or more arteries or blood flow passageways, such as, for example, abdominal aortic aneurysms or aortic occlusive disease, was effected by various surgical techniques, some of which involved the use of stent-grafts. The use of stent-grafts provided methods that were the least invasive and therefore involved less risk of infection and adverse patient reaction. However, use of prior art stent-graft structures typically required a minimum length of healthy tissue distance, or neck, between the the diseased portion of the artery, (such as the abdominal aortic aneurysm), and branch arteries (e.g., the renal arteries). This minimal neck length was specified to increase the possibility of a good seal between the prior art stent-graft structure and the wall of the major artery (e.g., the aorta) while at the same time allowing blood to flow to the intersecting branch arteries (e.g., the renal arteries). Typically, a neck length of approximately one and one-half centimeters was specified to use most prior art structures.

Unfortunately, many arterial diseases extended to closely approach or include the intersection of branching arteries or blood flow passageways, which diminishes or eliminates the available neck length, so they were untreatable or had to be treated by more invasive procedures (i.e., open surgery). However, the more invasive procedures, such as surgery, required that the patient be strong enough to survive the procedure, otherwise, treatment was postponed and/or withheld. Consequently, previously, many arterial diseases and aneurysms had to be either treated by more intrusive, and potentially dangerous, methods or, in some cases, the patient would simply have to wait until he or she was strong enough to potentially survive the surgery. Postponing or withholding treatment could result in a rupture of the arterial wall, and heavy hemorrhaging that often proves fatal. Consequently, waiting for treatment, or withholding treatment is not a desirable option.

To avoid more invasive surgery, or if surgery was not a viable option, doctors would consider using other prior art methods and structures in cases where the neck length was smaller than the specified minimum.

One prior method to address the situation where arterial disease occurred at the location of a branch arteries and where there was little or no arterial neck length between the diseased portion and the closest intersecting branch was to make a custom structure that would span the aneurysm and intersecting branch arteries (e.g., the renal arteries) and would thereby form a seal between the stent-graft and healthy tissue on the walls of the major artery (e.g., the aorta) above the aneurysm and intersecting branch arteries. However, in order to use this type of structure, fenestrations had to be custom made in the stent-graft to allow passage of blood to the intersecting branch arteries (e.g., the renal arteries).

In one prior art example, the procedure included placing a stent graft across the intersection of the aorta and the renal arteries. Preformed openings in the stent graft corresponds to the locations of the two branching renal arteries. Two secondary stent-grafts are then delivered and positioned in the side branches. This method required first precisely measuring, through imaging techniques, the exact location of the branch of the two renal arteries. To effectively use this method, the size or diameter of the two renal artery branches needed to be precisely measured and the lateral openings of the main graft and the open ends of the branch grafts had to be precisely sized so that once they were deployed and positioned in the respective main and branch arteries, they would fit to seal the aneurysm. Using this method, the main and branch stented grafts were then coupled to each other with a system of grooves and flanges or ribs, the grooves of one being received in the flange of the other to lock them together.

As discussed above, the prior art "solutions" to the little or no neck problem required a customized stent-graft structure having precisely measured and implemented features such as the longitudinal distance between branches, the radial positioning of the openings, and diameters of the openings. Consequently, the custom stent-grafts used with prior art techniques were not easily adaptable to mass production.

Because the custom made stent-grafts used with prior art techniques were custom made, there was considerable time lag between diagnosis and deployment of the stent-graft while waiting for the custom made stent-graft to be built. Since the aorta and renal arteries are comprised of living tissue, their physical dimensions, so critical to prior art methods, could change between when the measurements were taken and when the stent was deployed.

Custom stent-grafts used with the prior art required precise measurement and production techniques, were vulnerable to error, had to be special ordered well in advance of their use, and could not accommodate minor changes in the patient's physiology.

What is needed is a method and apparatus for treating arterial disease that can be more flexibly applied and can be used on short notice in a variety of situations and on a variety of anatomies.

SUMMARY OF THE INVENTION

In examples in accordance with the present invention, modular branch vessel stent-graft assemblies are assembled often in a patient's trunk/parent artery, from at least two components; a first component and a second component. The first and second components each include a first "window", or first fenestration, and a second window, or second fenestration. In one example, the first window is relatively large while the second window is smaller. In one example, the second component has a diameter smaller than the diameter of the first component so that the second component couples with the first component by fitting at least partially within the first component to form the modular branch vessel stent-graft assembly.

As the first and second components are assembled, the second component positioned relative to the first component so that the first component first window overlaps with the second component second window to form a first adjustable branch opening and the first component second window overlaps with the second component first window to form a second adjustable branch opening in the modular branch vessel stent-graft assembly. By selecting the relative longitudinal and radial positions of the first and second components of the modular branch vessel stent-graft assembly, the longitudinal and radial positions of the branch openings can be varied to meet the needs of the particular application.

In one example, a first component of a modular branch vessel stent-graft assembly includes a proximal, or first, end and a distal, or second, end connected by a first component body. A first component longitudinal axis L1 runs through the first component body from the proximal end to the distal end. In one example, the distal end is substantially cylindrical, as is the first component body, and the distal end and first component body have the same first diameter. The first component of the modular branch vessel stent-graft assembly includes a first component first window, or first component first fenestration, and a first component second window, or first component second fenestration. The first component first window is relatively large while the first component second window is smaller.

The first component body of the modular branch vessel stent-graft assembly includes a stent body mesh made of stainless steel, nitinol, or other materials, adapted to render the first component flexible and, as well, compressible for insertion into various delivery devices such as a catheter or lumen and attendant balloon. The first component body of the modular branch vessel stent-graft assembly also includes a graft comprised of a hollow tube of material, such as Dacron, ePTFE or polyurethane, that is typically positioned such that the stent body mesh and graft are coupled to form a hollow tubular structure making up the first component body.

A second component of a modular branch vessel stent-graft assembly includes a proximal, or first, end and a distal, or second, end connected by a second component body. A second component longitudinal axis L2 runs through second component body from the proximal end to the distal end. The distal end is substantially cylindrical, as is the second component body, and the distal end and first component body have the same second diameter. The second diameter can be smaller than or approximately equal to the first diameter discussed above. The second component of the modular branch vessel stent-graft assembly includes a second component first window, or second component first fenestration, and a second component second window, or second component second fenestration. The second component first window is relatively large while the second component second window is smaller.

In another example in accordance with the present invention, the second component body of the modular branch vessel stent-graft assembly includes a stent body mesh made of stainless steel, nitinol, or other similar materials, adapted to render the second component flexible and, as well, capable of being compressed for insertion into various delivery devices such as a catheter or lumen. The second component body of the modular branch vessel stent-graft assembly also includes a graft comprised of a hollow tube of material, such as Dacron, ePTFE or polyurethane, that is typically positioned such that the stent body mesh and graft are coupled to form a hollow tubular structure making up the second component body.

As discussed above, at least a portion of the body of the second component of the modular branch vessel stent-graft assembly, fits within at least a portion of the body of the first component of modular branch vessel stent-graft assembly.

The second component is coupled with the first component to form modular branch vessel stent-graft assembly by placing the distal end of the second component of modular branch vessel stent-graft assembly inside the proximal end of the first component of the modular branch vessel stent-graft assembly such that the first component longitudinal axis L1 is coaxial with the second component longitudinal axis L2.

The first and second components are assembled into the modular branch vessel stent-graft assembly as the first and second components are deployed into a patient's parent artery. As discussed above, as the first and second components are deployed, the second component is adjusted relative to the first component so that the first component first window overlaps with the second component second window to form a first adjustable branch opening and the first component second window overlaps with the second component first window to form a second adjustable branch opening in the modular branch vessel stent-graft assembly. By adjusting the relative longitudinal and radial positions of the first and second components of the modular branch vessel stent-graft assembly, the longitudinal and radial positions of the adjustable branch openings can be varied to meet the needs of the particular application.

As discussed above the longitudinal positioning of the branch openings is adjustable. In addition, the angular positioning of the branch openings is also adjustable. Consequently, in contrast to prior art methods and structures, the modular branch vessel stent-graft assemblies of the invention do not need to have the degree of customization previously required where a device is custom made for each patient.

In addition, using the modular branch vessel stent-graft assemblies according to the invention, it not necessary to obtain the number exact measurements that were required to build the custom stent-grafts used with prior art techniques. Consequently, there is less opportunity to introduce human error in both the measurement taking process.

In addition, the modular branch vessel stent-graft assemblies according to the invention have some flexibility to accommodate changes in the patient's physiology over time.

DETAILED DESCRIPTION

Figure 1A:
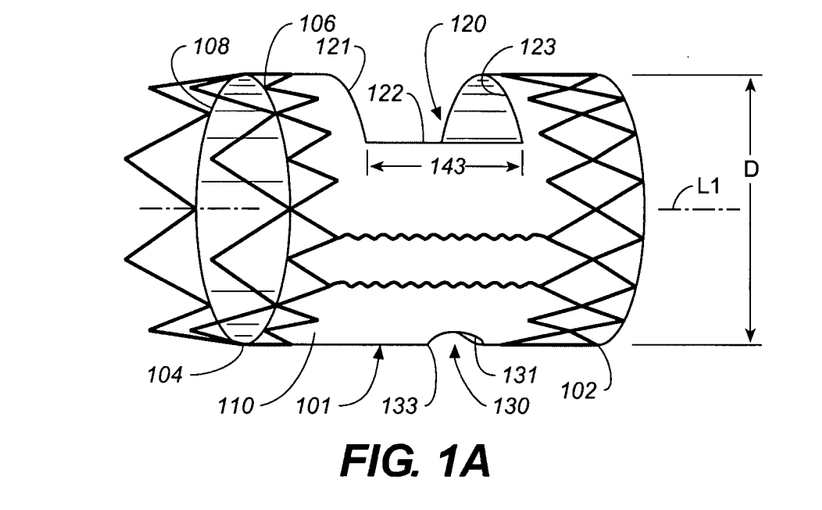
FIG. 1A is a side perspective-like view of a first component of a modular branch vessel stent-graft assembly.
Figure 1B:
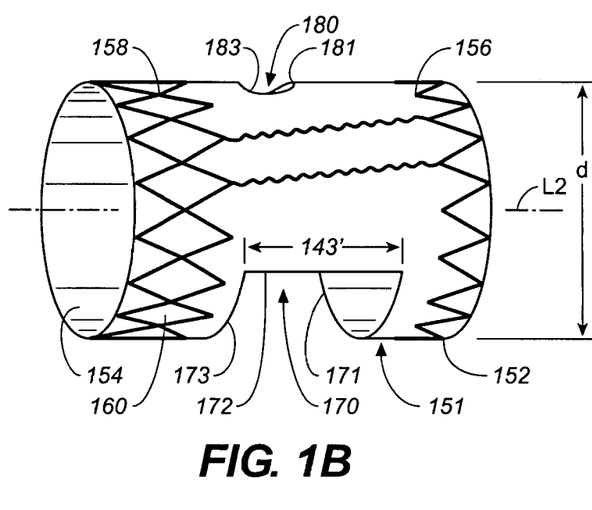
FIG. 1B is a side perspective-like view of a second component of a modular branch vessel stent-graft assembly.

In examples in accordance with the present invention, modular branch vessel stent-graft assemblies (100 in FIGS. 1C to 1G, and 2) are assembled, often in a patient's trunk/parent artery (201 in FIG. 2), from at least two components; a first component (101 in FIG. 1A) and a second component (151 in FIG. 1B). The first and second components each include a first window, or first fenestration, (120, 170) and a second window, or second fenestration (130, 180). The first windows (120, 170) are relatively large while the second windows (130, 180) are relatively smaller.

As the first and second components are assembled, the second component can be adjusted relative to the first component so that the first component first window overlaps with the second component second window to form a first adjustable branch opening (191 in Figs. 1E to 1G, and 2) and the first component second window overlaps with the second component first window to form a second branch opening (193 in Figs. 1E to 1G, and 2) in the modular branch vessel stent-graft assembly. By adjusting the relative longitudinal and angular positions of the first and second components of the modular branch vessel stent-graft assembly, the longitudinal and angular positions of the adjustable branch openings can be varied to meet the needs of the particular application.

The first and second components are assembled into the modular branch vessel stent-graft assembly as the first and second components are deployed into a patient's parent artery. The first component is fully deployed and then the second component is deployed.

As discussed above the longitudinal positioning of the branch openings is adjustable. In addition, the angular positioning of the branch openings is also adjustable. In contrast to prior art methods and structures, the modular branch vessel stent-graft assemblies of the invention do not need to be custom made for each patient. Therefore, the modular branch vessel stent-graft assemblies of the invention can be mass-produced with minimal labor.

FIG. 1A and FIG. 1B together show front perspective-like views of the components 101 and 151 of a modular branch vessel stent-graft assembly 100. In particular, FIG. 1A is a perspective-like view of one example of a first component 101 and FIG. 1B is a perspective-like view of one example of a second component 151 of modular branch vessel stent-graft assembly 100.

As shown in FIG. 1A, first component 101 of modular branch vessel stent-graft assembly 100 is a substantially circular cylinder and includes a proximal, e.g., first, end 104 and a distal, e.g., second, end 102 connected by a generally circularly cylindrical body 106. Further, as shown in FIG. 1A, first component 101 of modular branch vessel stent-graft assembly 100 has a longitudinal axis L1 running through body 106 from proximal end 104 to distal end 102.

Distal end 102 is substantially cylindrical. Body 106 is substantially cylindrical and distal end 102 and body 106 have the same diameter D. However, in alternative examples, portions (not shown) of a body (e.g., 106) may have a diameter greater than or less than the diameter of distal end 104.

In addition, as shown in FIG. 1A, first component 101 of modular branch vessel stent-graft assembly 100 includes a first component first window, or first component first fenestration, 120. First component first window 120 is a rectangular window cut out portion in body 106 through to the interior right circular cylinder wall 121. First component first window 120 includes a radial window perimeter 123 and a longitudinal window perimeter 122. Radial window perimeter 123 has an angular opening of between 60 and 125 degrees taken from the axis L1. Side length 143 of longitudinal window perimeter 122 is between 0.5 inch and 2.0 inches. However, as will be readily apparent to those of skill in the art from the discussion below, the values of radial window perimeter 123 and longitudinal window perimeter side length 143 of first component first window 120 can be any values desired by the manufacturer or the end user of modular branch vessel stent-graft assembly 100.

In addition, while first component first window 120 is described above, and shown in FIG. 1A, as a substantially rectangular lateral opening with substantially straight longitudinal window perimeter side length 143, those of skill in the art will readily recognize that first component first window 120 can be constructed in any shape desired, including but not limited to: circular, oval, square, or diamond.

As also shown in FIG. 1A, first component 101 of modular branch vessel stent-graft assembly 100 includes a first component second window, or first component second fenestration, 130. First component second window 130 is a circular cylindrical cut out portion in body 106 through to the interior right circular cylinder wall 131. In one example in accordance with the present invention, first component second window 130 includes a radial window perimeter 133. First component second window 130 is significantly smaller than first component first window 120 and is of a generally circular shape that has a similar geometry similar to the geometry of the associated complementary vessel ostia. However, first component second window 130 can be constructed in any shape desired, including but not limited to: circular, oval, square, or diamond.

As shown in FIG. 1A, body 106 of first component 101 of modular branch vessel stent-graft assembly 100 includes a stent body mesh (or stent ring) 108 made of stainless steel, nitinol, or other similar materials, adapted to render first component 101 of modular branch vessel stent-graft assembly 100 flexible and, as well, capable of being compressed into a catheter for insertion into various delivery devices such as a catheter or lumen. As discussed below, these delivery systems are well known in the art. Moreover, it is also well known in the art to construct stented grafts of various materials such as stainless steel or nitinol, capable of being compressed in size by stress or temperature and, upon delivery to a diseased artery, capable of being formed to a given size and shape.

In one example in accordance with the present invention, body 106 of first component 101 of modular branch vessel stent-graft assembly 100 also includes a graft material 110 comprised of a hollow tube, such as Dacron, ePTFE or polyurethane, that is typically positioned such that stent body mesh 108 and graft 110 are coupled to form the hollow tubular structure making up body 106.

FIG. 1B shows a side perspective-like view of second component 151 of modular branch vessel stent-graft assembly 100 which is substantially cylindrical and includes a proximal, e.g., first, end 154, a distal, e.g., second, end 152 connected by a body 156. Further, as shown in FIG. 1B, second component 151 of modular branch vessel stent-graft assembly 100 has a longitudinal axis L2 running through body 156 from proximal end 154 to distal end 152.

In one example, proximal end 154 is substantially cylindrical, body 156 is substantially cylindrical and distal end 152 is substantially cylindrical. In one example, proximal end 154 includes a bare spring (not shown) to provide radial strength to proximal end 154. In one example, proximal end 154, distal end 152, and body 156 have the same diameter d. However, in alternative examples, a portion (not shown) of body (e.g., 156) has a diameter greater than or less than the diameter d of distal end (e.g., 152).

As shown in FIG. 1B, body 156 of second component 151 of modular branch vessel stent-graft assembly 100 includes a stent body mesh 158 made of stainless steel, nitinol, or other similar materials, adapted to render second component 151 of modular branch vessel stent-graft assembly 100 flexible and, as well, capable of being compressed for insertion into various delivery devices such as a catheter or lumen and attendant balloon (not shown). Moreover, it is also known in the art to construct stented grafts of various materials such as stainless steel or nitinol, capable of being compressed or reduced in size by stress or temperature and, upon delivery to a diseased artery, capable of being expanded to a given size and shape.

Body 156 of second component 151 of modular branch vessel stent-graft assembly 100 also includes a hollow tube of graft material 160 comprised of Dacron, that is typically sewn to the stent structures and expanded through the use of a balloon catheter (not shown) or retraction of a covering sheath when a self expanding stent structure is used to form the hollow tubular structure of body 156.

As shown in FIG. 1B, second component 151 of modular branch vessel stent-graft assembly 100 also includes a second component first window, or second component first fenestration, 170, second component first window 170 is a rectangular cut out portion in body 160 that is cut through to interior right circular cylinder wall 171. Second component first window 170 includes a radial window perimeter 173 and a longitudinal window perimeter 172. Radial window perimeter 173 has an angular opening taken from the center axis L2 of between 60 and 125 degrees and a length of a side length 143' of longitudinal window perimeter 172 is between 0.5 inch and 2.0 inches, however, as will be apparent to those of skill in the art from the discussion below, the values of radial window perimeter 173 and longitudinal window perimeter side length 143' of second component first window 170 can be any values desired by the manufacturer or the end user of modular branch vessel stent-graft assembly 100.

In addition, while second component first window 170 is described above, and shown in FIG. 1B, as a substantially rectangular lateral opening with substantially straight longitudinal window perimeter side length 143', those of skill in the art will readily recognize that second component first window 170 can be constructed in any shape desired, including but not limited to, circular, oval, square, or diamond.

As also shown in FIG. 1B, second component 151 of modular branch vessel stent-graft assembly 100 includes a second component second window, or second component second fenestration, 180. Second component second window 180 is a circular cylindrical cut out portion in body 160 that exposes interior right circular cylinder wall 181. Second component second window 180 includes a radial window perimeter 183. Second component second window 180 is significantly smaller than second component first window 170 and is of a generally circular shape. However, those of skill in the art will recognize that second component second window 180 can be constructed in any shape desired, including but not limited to, circular, oval, square, or diamond.

Figure 1C:
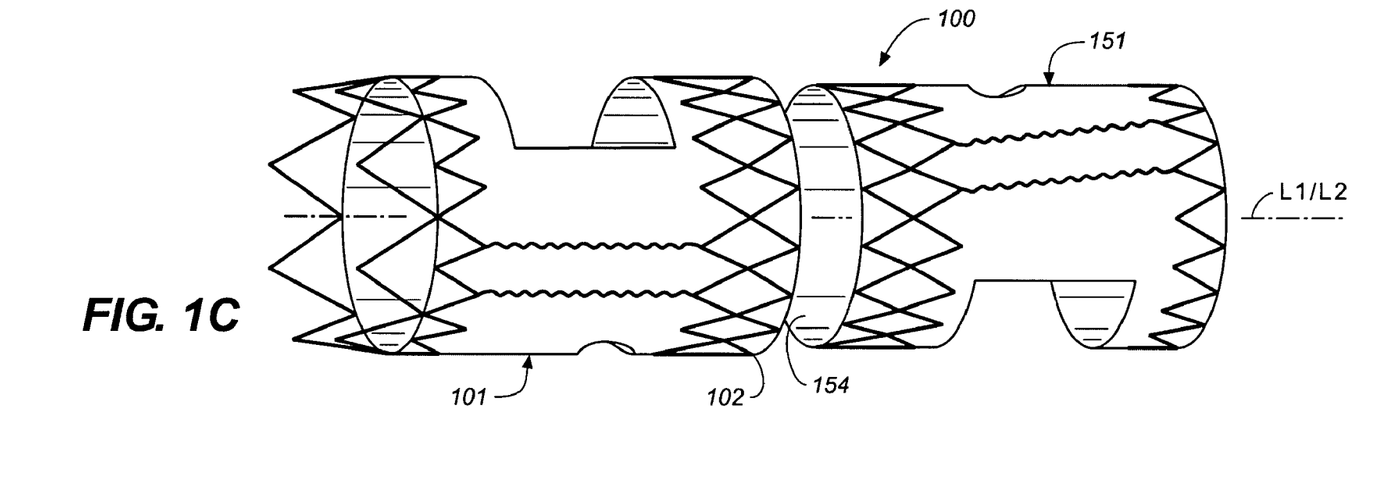
FIG. 1C is a side perspective-like view of the second component of FIG. 1B placed in alignment with the first component of FIG. 1A, prior to the coupling of the second component of FIG. 1B with the first component of FIG. 1A.

As shown in FIG. 1C, in one example, second component 151 is placed in alignment with first component 101 of modular branch vessel stent-graft assembly 100 such that proximal end 154 of second component 151 of modular branch vessel stent-graft assembly 100 is adjacent to distal end 102 of first component 101 of modular branch vessel stent-graft assembly 100 and longitudinal axis L1 of first component 101 of modular branch vessel stent-graft assembly 100 is generally aligned with longitudinal axis L2 of second component 151 of modular branch vessel stent-graft assembly 100 to form co-axis L2/L1. In one example, first component 101 is positioned and fully deployed and then second component 151 is deployed inside the first component while FIG. 1C shows an illustration of components side by side, but never encountered in practice.

Figure 1D:
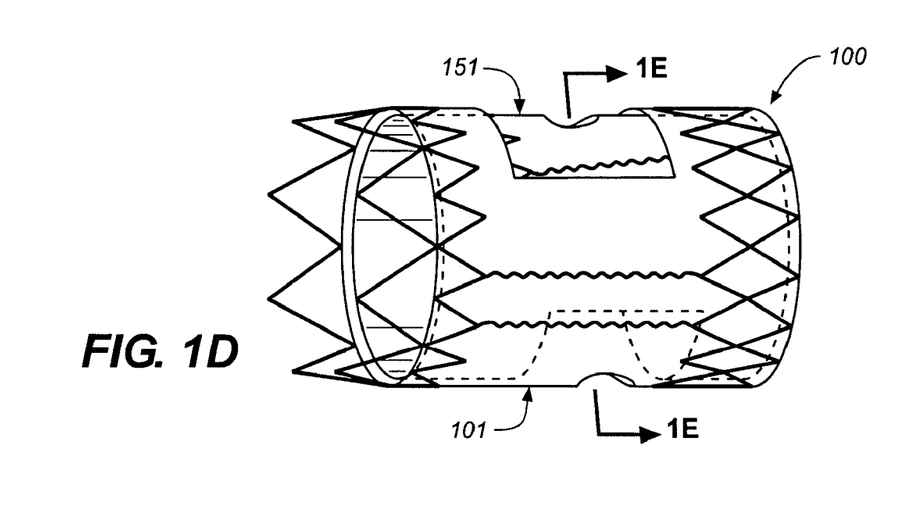
FIG. 1D is a side perspective-like view of the second component of FIG. 1B coupled with the first component of FIG. 1A to form a modular branch vessel stent-graft assembly.

As shown in FIG. 1D, when second component 151 of modular branch vessel stent-graft assembly 100 is coupled with first component 101 of modular branch vessel stent-graft assembly 100, proximal end 154, and at least a portion of second component 151 of modular branch vessel stent-graft assembly 100, is positioned within distal end 102 and body 106 of first component 101 of modular branch vessel stent-graft assembly 100. The selectively adjustable coupling and deployment of second component 151 of modular branch vessel stent-graft assembly 100 with first component 101 of modular branch vessel stent-graft assembly 100 results in locating neighboring branch vessel ostiums opposite similar sized or deployment branch fenestrations 191 and 193 in modular branch vessel stent-graft assembly 100.

In one example in accordance with the present invention, the position of adjustable branch opening 191, synonymous with second window 130 location in the first component 101 is variable and can be selectively positioned as the first component 101 of modular branch vessel stent-graft assembly 100 is deployed within the main artery (lumen) while taking care to align the second window opening 130 (191) with the corresponding branch. Radiopaque markers (not shown) are used to position the components and their openings, by methods well known to those of skill in the art.

The angular and longitudinal positioning of second adjustable branch opening 193 with respect to first branch opening 191, is variable and can be selected by increasing or decreasing how far second component 151 of modular branch vessel stent-graft assembly 100 is deployed within proximal end 102 of first component 101 of modular branch vessel stent-graft assembly 100.

Figure 1E:
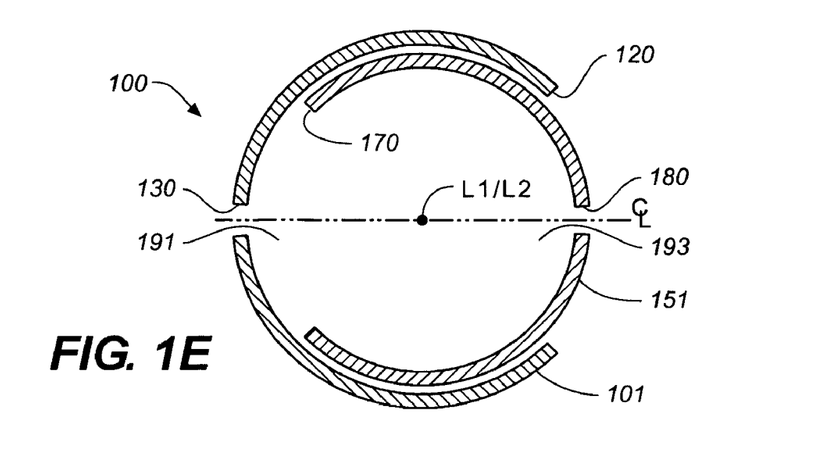
FIG. 1E is a cross-sectional view of a second component of the modular branch vessel stent-graft assembly coupled with the first component in FIG. 1D when the branch openings are opposite one another as seen at 1E-1E in FIG. 1D.
Figure 1F:
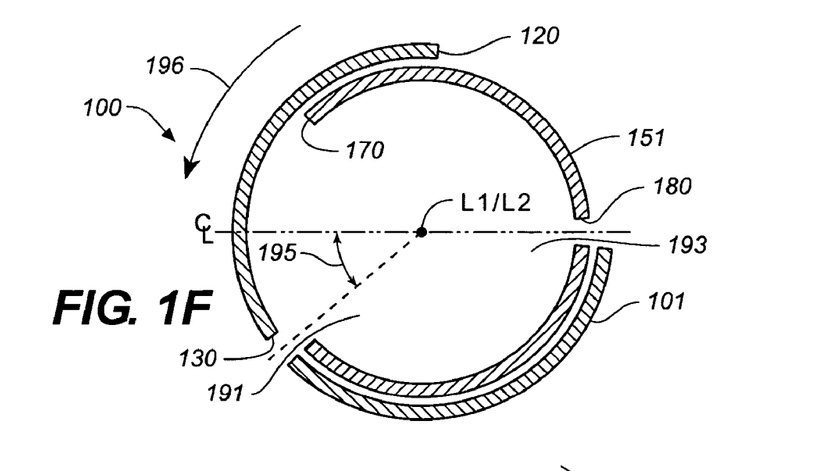
FIG. 1F is a cross-sectional view of a second component of the modular branch vessel stent-graft assembly coupled with the first component as would be seen along 1E-1E in FIG. 1D when the first component is rotated around the common axis.
Figure 1G:
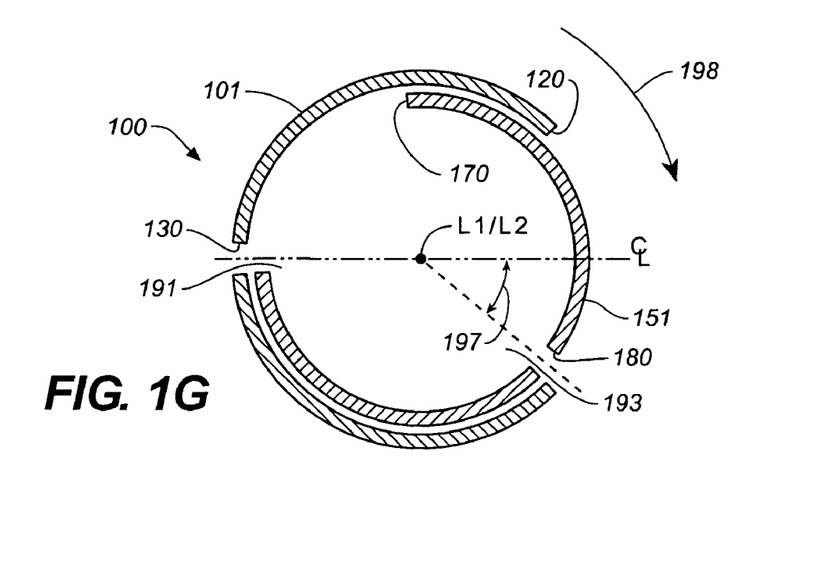
FIG. 1G is a cross-sectional view of a second component of the modular branch vessel stent-graft assembly coupled with the first component as would be seen along 1E-1E in FIG. 1D when the second component is rotated around the common axis.

As shown in FIGS. 1E, 1F, and 1G, the angular position of adjustable branch opening 191 can be selected by predeployment rotation of second component 151 of modular branch vessel stent-graft assembly 100 in either the direction about common radial axis L2/L1. FIG. 1E is a cross-sectional view of second component 151 coupled with first component 101 cut along line 1E-1E in FIG. 1D where opening first (191) and second (193) are directly across from one another. FIG. 1F is a cross-sectional view of second component 151 coupled with first component 101 as seen along 1E-1E in FIG. 1D where first component 101 is shown in a position different from that shown in FIG. 1E where during or prior to deployment the first component 101 was rotated through an angle 195 along axis L1/L2 in direction 196.

As discussed above, the angular position of first adjustable branch opening 191 is selected by predeployment rotation of first component 101 of modular branch vessel stent-graft assembly 100 in either the direction about common radial axis L2/L1. Those of skill in the art will readily recognize that the angular position of second adjustable branch opening 193 can also be adjusted by predeployment rotation of second component 151 of modular branch vessel stent-graft assembly 100 about common radial axis L2/L1.

As shown in FIGS. 1E, 1F, and 1G, the angular position of second adjustable branch opening 193 can be set within a range of angles by predeployment rotation of second component 151 of modular branch vessel stent-graft assembly 100 in either the direction about common radial axis L2/L1. FIG. 1E is a cross-sectional view of second component 151 coupled with first component 101 as seen along 1E-1E in FIG. 1D. FIG. 1G is a cross-sectional view of second component 151 coupled with first component 101. As can be seen second component 151 has been predeployment rotated through an angle 197 along axis L1/L2 with respect to first component 101 in direction 198.

As shown above, modular branch vessel stent-graft assembly 100, in contrast to the prior art structures and methods, provides for variable positioning longitudinal and angular positioning of first and second adjustable branch openings 191 and 193. Consequently, modular branch vessel stent-graft assembly 100 can be assembled from first component 101 and second component 151 in situ. The position, length and width of first and second adjustable branch openings 191 and 193 can be modified to locate first and second adjustable branch openings 191 and 193 at the exact locations needed, and to match the general dimensions and geometry needed, to meet the particular needs of the patient, and the artery structure, being repaired.

Figure 2:
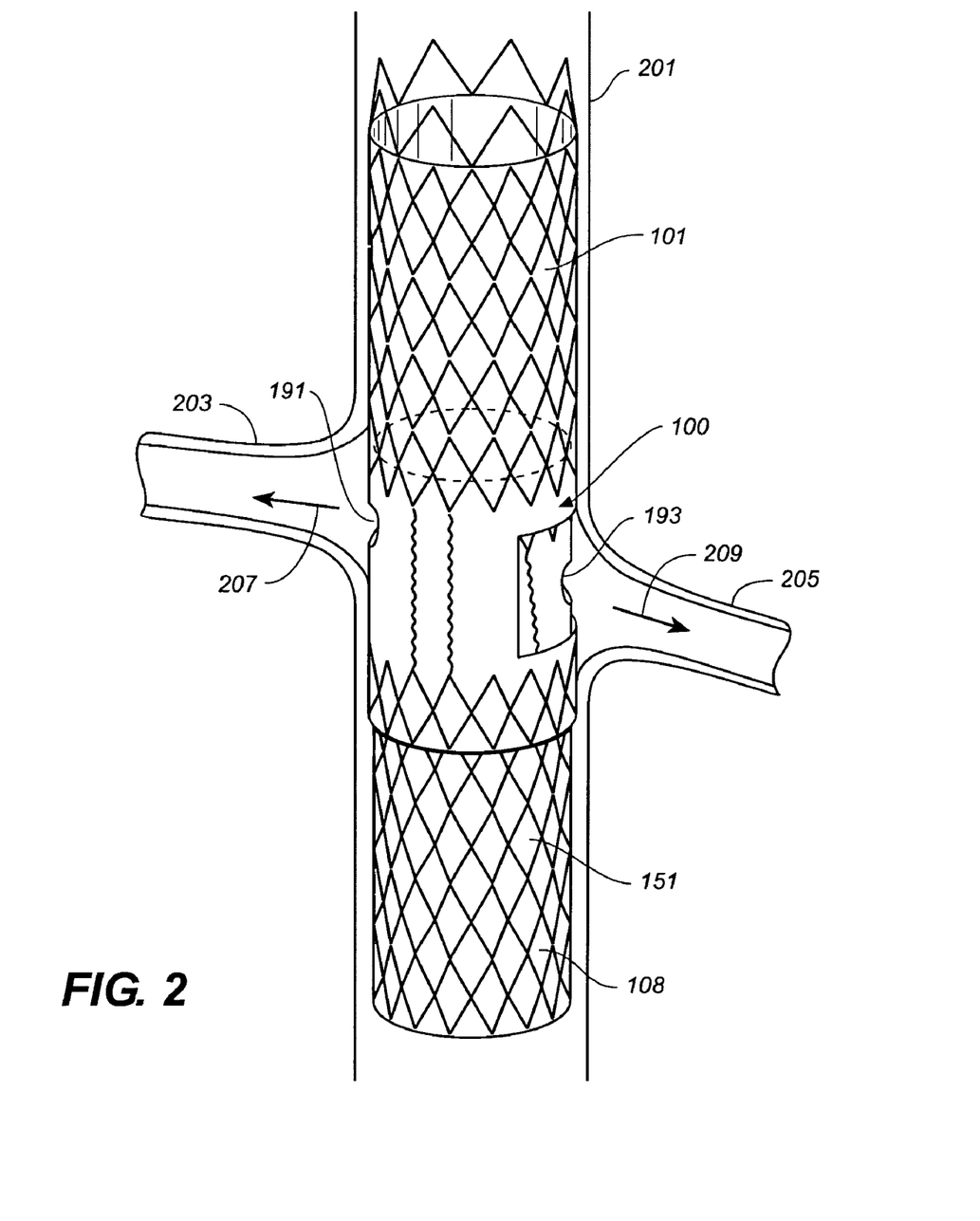
FIG. 2 is a side partial cutaway view of a body lumen containing an aneurysm with a modular branch vessel stent-graft assembly including the attributes as shown in the device pictured in FIGS. 1A to 1G deployed.

FIG.2 is a side partial cutaway view of a body lumen 201, also referred to herein as trunk/parent artery 201, in one example the aorta, containing an aneurysm (not shown), in one example an abdominal aortic aneurysm. As shown in FIG.2A, a modular branch vessel stent-graft assembly having feature of the device shown in FIGS. 1A to 1G are deployed with adjustable branch openings 191 and 193 positioned to provide blood flow to the patient's branch arteries 203 and 205, in one example the renal arties, in the direction shown by arrows 207 and 209, respectively.

Modular branch vessel stent-graft assembly 100 can be deployed by standard methods known to those of skill in the art. First component 101 of modular branch vessel stent-graft assembly 100 is deployed first, either as a self-expanding structure or as a balloon expandable structure, by methods well known to those of skill in the art. In one example, first component 101 of modular branch vessel stent-graft assembly 100 is at first only partially deployed by methods well known to those of skill in the art, such as only partially pulling back a deployment sheath (not shown), and then first component 101 of modular branch vessel stent-graft assembly 100 is manipulated to the desired position. In this example, once first component 101 of modular branch vessel stent-graft assembly 100 is positioned as desired, first component 101 of modular branch vessel stent-graft assembly 100 is fully deployed by fully removing the deployment sheath (not shown).

Once first component 101 of modular branch vessel stent-graft assembly 100 is fully positioned and deployed as described above, second component 151 of modular branch vessel stent-graft assembly 100 is also deployed by methods well known to those of skill in the art, either as a self-expanding structure or by balloon expandable structure. Second component 151 of modular branch vessel stent-graft assembly 100, like first component 101 of modular branch vessel stent-graft assembly 100, is at first only partially deployed by methods well known to those of skill in the art, such as by partially pulling back a deployment sheath (not shown), and then second component 151 of modular branch vessel stent-graft assembly 100 is manipulated to provide first and second adjustable branch openings 191 and 193 with the desired position and dimensions as discussed above with respect to FIGS. 1E to 1G.

Radiopaque markers (not shown) on second component 151 of modular branch vessel stent-graft assembly 100 are used to position second component 151 of modular branch vessel stent-graft assembly 100. Once second component 151 of modular branch vessel stent-graft assembly 100 is fully deployed, second component 151 of modular branch vessel stent-graft assembly 100 and first component 101 of modular branch vessel stent-graft assembly 100 are held in position by a frictional interference fit or inter-engagement. Second component 151 of modular branch vessel stent-graft assembly 100 and first component 101 of modular branch vessel stent-graft assembly 100 are sized, i.e., the diameters D and d in FIG. 1A are chosen, such that, once fully deployed and assembled into modular branch vessel stent-graft assembly 100 interaction between second component 151 of modular branch vessel stent-graft assembly 100 and first component 101 of modular branch vessel stent-graft assembly 100 creates a frictional force through their radial interference.

Those of skill in the art will readily recognize that while the discussion above, and FIG. 2, is directed to the specific example where the arterial disease is an abdominal aortic aneurysm, the modular branch vessel stent-graft assembly 100 of the invention maybe deployed to treat any arterial or vascular disease where two or more vessels or arteries or blood flow passageways branch.

In some instances, it may be necessary to provide additional support to branch arteries 203 and 205 and to provide a better seal between adjustable branch openings 191 and 193 and branch arteries 203 and 205. In these instances, a branch stent-graft (not shown) can be used with modular branch vessel stent-graft assembly 100. In other examples, a branch structure can be used with second component 151 of modular branch vessel stent-graft assembly 100 and first component 101 of modular branch vessel stent-graft assembly 100 to provide additional support to branch arteries 203 and 205 and to direct/channel the flow of blood from first and second adjustable branch openings 191 and 193 into branch arteries 203 and 205.

As noted above, in some instances, it may be necessary to provide additional support to branch arteries 203 and 205 and to direct flow of blood from first and second adjustable branch openings 191 and 193 into branch arteries 203 and 205. In these instances, a branch stented graft structure can be used with modular stent graft assembly 100.

Figure 3:
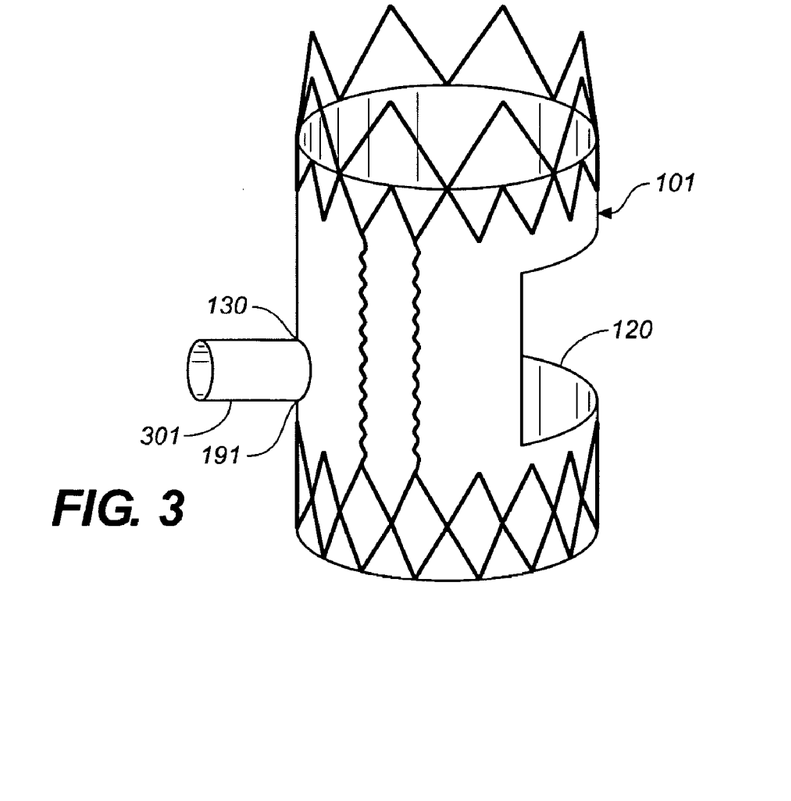
FIG. 3 shows a perspective-like view of another embodiment of a typical branch stent graft structure suitable for use in one example according to the invention.
Figure 4:
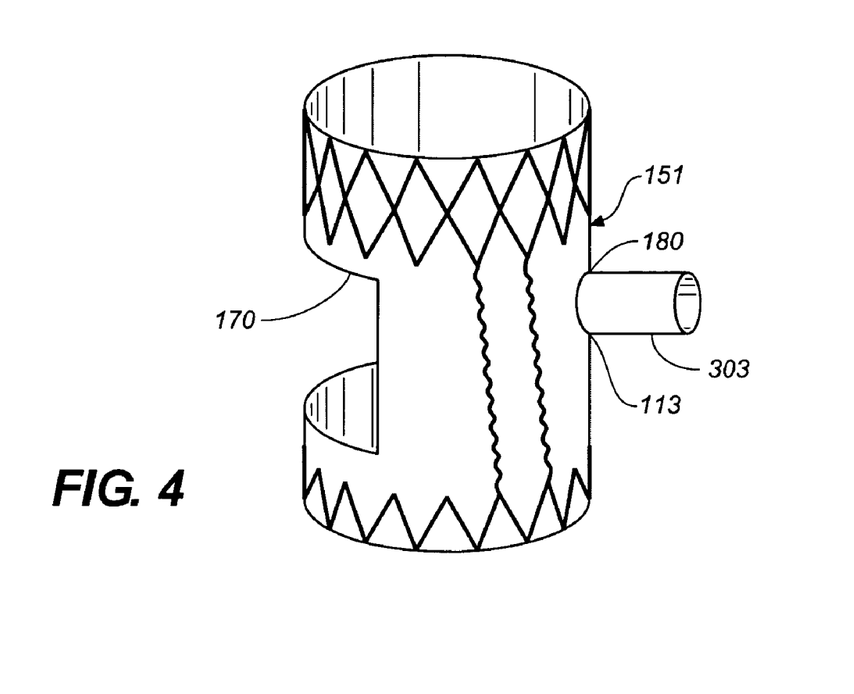
FIG. 4 shows a modular branch vessel stent-graft assembly with branch structures attached to the branch openings, complimentary with the one shown in FIG. 3.

FIG.3 shows one example of a modular branch vessel stent-graft assembly 100 with first and second integral branch structures 301 and 303 attached to adjustable branch openings 191, 193. First and second integral branch structures 301 and 303 are made of Dacron, ePTFE, polyurethane or a similar material. Integral branch structures 301 and 303 are deployed to extend into branch arteries 203 and 205 to provide additional support to branch arteries 203 and 205 and to channel the flow of blood from first and second adjustable branch openings 191 and 193 into branch arteries 203 and 205. Like first and second adjustable branch openings 191 and 193, first and second integral branch structures 301 and 303 can be predeployment positioned both longitudinally and angularly within the trunk/parent artery.

This disclosure also includes a method of deployment of the modular branch vessel stent-graft assembly, wherein; said attached branch structures are telescoping attached branch structures. A method of deploying a multi component branch stent graft structure consisting of the steps of deploying a first cylindrical component having a large first window approximately radially opposed to a second window substantially smaller than the first window, the first and second windows each creating an opening through a wall of the first cylindrical component in a body lumen where the second window is selectively located to match with a first branch vessel branching from the body lumen and then, deploying in a second cylindrical component having a large first window approximately radially opposed to a second window substantially smaller than the first window, the first and second windows each creating an opening through a wall of the second cylindrical component within the first cylindrical component where the second window of the second cylindrical component is selectively located to match a second branch vessel branching from the body lumen and located within the large first window of the first cylindrical component.

This disclosure provides exemplary examples in accordance with the present invention. The scope of the present invention is not limited by these exemplary examples. Consequently, the invention is not intended to be limited to the specific examples discussed above.

What is claimed is:

1. A modular branch vessel stent-graft assembly comprising:
    a first component, said first component comprising:
    a first component proximal end with a first component proximal end opening;
    a first component distal end with a first component distal end opening;
    a first component body connecting said first component proximal end and said first component distal end; and
    a first component first window formed in said first component body;
    a first component second window formed in said first component body;
    a second component, said second component comprising:
    a second component proximal end with a second component proximal end opening;
    a second component distal end with a second component distal end opening;
    a second component body connecting said second component proximal end and said second component distal end; and
    a second component first window formed in said second component body, said second component first window being larger than said first component second window;
    a second component second window formed in said second component body, said first component first window being larger than said second component second window;
    said second component distal end and at least a portion of said second component body being positioned within said first component proximal end and at least a portion of said first component body to form said modular branch vessel stent-graft assembly; and
    an overlap of said second component second window and said first component first window and said second component first window and said first component second window forming two adjustable branch openings in said modular branch vessel stent-graft assembly.

2. The modular branch vessel stent-graft assembly of claim 1, wherein;
    at least one of said adjustable branch openings in said modular branch vessel stent-graft assembly has a longitudinal position along a longitudinal axis of said modular branch vessel stent-graft assembly that is adjustable by moving said second component of said modular branch vessel stent-graft assembly with respect to said first component of said modular branch vessel stent-graft assembly along said longitudinal axis of said modular branch vessel stent-graft assembly.

3. The modular branch vessel stent-graft assembly of claim 2, wherein;
    at least one of said adjustable branch openings in said modular branch vessel stent-graft assembly has an angular position about said longitudinal axis of said modular branch vessel stent-graft assembly that is predeployment adjustable by rotating said second component of said modular branch vessel stent-graft assembly with respect to said first component of said modular branch vessel stent-graft assembly around said longitudinal axis of said modular branch vessel stent-graft assembly.

4. The modular branch vessel stent-graft assembly of claim 3, wherein;
    at least one of said adjustable branch openings in said modular branch vessel stent-graft assembly has an angular position about said longitudinal axis of said modular branch vessel stent-graft assembly that is adjustable by predeployment rotating said first component of said modular branch vessel stent-graft assembly and predeployment rotating said second component of said modular branch vessel stent-graft assembly around said longitudinal axis of said modular branch vessel stent-graft assembly.

5. The modular branch vessel stent-graft assembly of claim 4, wherein;
    said first component body connecting said first component proximal end and said first component distal end comprises a stent body mesh coupled to a graft; and
    said second component body connecting said second component proximal end and said second component distal end comprises a stent body mesh coupled to a graft.

6. The modular branch vessel stent-graft assembly of claim 5, wherein;
    said first component body connecting said first component proximal end and said first component distal end is substantially cylindrical and said first component proximal end opening is substantially cylindrical with a first diameter; and
    said second component body connecting said second component proximal end and said second component distal end is substantially cylindrical and said second component proximal end opening is substantially cylindrical with a second diameter, further wherein;
    said first diameter is greater than said second diameter.

7. The modular branch vessel stent-graft assembly of claim 1, wherein;
    a first adjustable branch opening of said two adjustable branch openings is longitudinally offset from a second adjustable branch opening of said two adjustable branch openings an offset distance along a longitudinal axis of said second component body.

8. The modular branch vessel stent-graft assembly of claim 7, wherein;
    said first adjustable branch opening in said modular branch vessel stent-graft assembly has a longitudinal position along a longitudinal axis of said modular branch vessel stent-graft assembly that is predeployment adjustable by moving said second component of said modular branch vessel stent-graft assembly with respect to said first component of said modular branch vessel stent-graft assembly along said longitudinal axis of said modular branch vessel stent-graft assembly.

9. The modular branch vessel stent-graft assembly of claim 1
    wherein said first component second window includes a first component branch structure attached to said first component and
    said second component second window includes a second component branch structure attached to said second component.

10. The modular branch vessel stent-graft assembly of claim 9, wherein;
at least one of said adjustable branch openings in said modular branch vessel stent-graft assembly has a longitudinal position along a longitudinal axis of said modular branch vessel stent-graft assembly that is predeployment adjustable by moving said second component of said modular branch vessel stent-graft assembly with respect to said first component of said modular branch vessel stent-graft assembly along said longitudinal axis of said modular branch vessel stent-graft assembly.

11. The modular branch vessel stent-graft assembly of claim 10, wherein;
at least one of said adjustable branch openings in said modular branch vessel stent-graft assembly has an angular position about said longitudinal axis of said modular branch vessel stent-graft assembly that is adjustable by rotating said second component of said modular branch vessel stent-graft assembly with respect to said first component of said modular branch vessel stent-graft assembly around said longitudinal axis of said modular branch vessel stent-graft assembly.

12. The modular branch vessel stent-graft assembly of claim 11, wherein;
at least one of said adjustable branch openings in said modular branch vessel stent-graft assembly has an angular position about said longitudinal axis of said modular branch vessel stent-graft assembly that is adjustable by rotating said first component of said modular branch vessel stent-graft assembly with respect to said second component of said modular branch vessel stent-graft assembly around said longitudinal axis of said modular branch vessel stent-graft assembly.

13. The modular branch vessel stent-graft assembly of claim 12, wherein;
said first component body connecting said first component proximal end and said first component distal end comprises a stent body mesh coupled to a graft; and
said second component body connecting said second component proximal end and said second component distal end comprises a stent body mesh coupled to a graft.

14. The modular branch vessel stent-graft assembly of claim 13, wherein;
said first component body connecting said first component proximal end and said first component distal end is substantially cylindrical and said first component proximal end opening is substantially cylindrical with a first diameter; and
said second component body connecting said second component proximal end and said second component distal end is substantially cylindrical and said second component proximal end opening is substantially cylindrical with a second diameter, further wherein;
said first diameter is greater than said second diameter.

15. The modular branch vessel stent-graft assembly of claim 9, wherein;
a first adjustable branch opening of said two adjustable branch openings is longitudinally offset from a second adjustable branch opening of said two adjustable branch openings an offset distance along a longitudinal axis of said second component body.

16. The modular branch vessel stent-graft assembly of claim 15, wherein;
said first adjustable branch opening in said modular branch vessel stent-graft assembly has a longitudinal position along a longitudinal axis of said modular branch vessel stent-graft assembly that is adjustable by moving said second component of said modular branch vessel stent-graft assembly with respect to said first component of said modular branch vessel stent-graft assembly along said longitudinal axis of said modular branch vessel stent-graft assembly.

17. A method of deploying a multi component branch stent graft structure consisting of the steps of:
deploying a first component in a body lumen, said first component comprising:
a first component proximal end with a first component proximal end opening;
a first component distal end with a first component distal end opening;
a first component body connecting said first component proximal end and said first component distal end;
a first component first window formed in said first component body; and
a first component second window formed in said first component body, where said first component second window is selectively located to match with a first branch vessel branching from said body lumen and then,
deploying a second component, said second component comprising:
a second component proximal end with a second component proximal end opening;
a second component distal end with a second component distal end opening;
a second component body connecting said second component proximal end and said second component distal end;
a second component first window formed in said second component body, said second component first window being larger than said first component second window; and
a second component second window formed in said second component body, said first component first window being larger than said second component second window, said deploying a second component comprising positioning said second component distal end and at least a portion of said second component body within said first component proximal end and at least a portion of said first component body such that an overlap of said second component second window and said first component first window and said second component first window and said first component second window form two adjustable branch openings,
where said second component second window is selectively located to match a second branch vessel branching from said body lumen.

* * * * *